US012749590B2

(12) United States Patent
Bouhnik et al.

(10) Patent No.: US 12,749,590 B2
(45) Date of Patent: Sep. 29, 2026

(54) IMAGING SYSTEM COLLIMATOR FOR HIGH ENERGY AND LOW ENERGY ISOTOPES

(71) Applicant: GE Precision Healthcare LLC, Waukesha, WI (US)

(72) Inventors: Jean-Paul Bouhnik, Haifa (IL); Yariv Grobshtein, Haifa (IL); Netanella Didi, Haifa (IL); Yaron Hefetz, Tirat Carmel (IL)

(73) Assignee: GE PRECISION HEALTHCARE LLC, Waukesha, WI (US)

(*) Notice: Subject to any disclaimer, the term of this patent is extended or adjusted under 35 U.S.C. 154(b) by 118 days.

(21) Appl. No.: 18/934,127

(22) Filed: Oct. 31, 2024

(65) Prior Publication Data

US 2026/0120909 A1 Apr. 30, 2026

(51) Int. Cl.
*G21K 1/02* (2006.01)
*A61B 6/03* (2006.01)
(Continued)

(52) U.S. Cl.
CPC .............. *G21K 1/025* (2013.01); *A61B 6/037* (2013.01); *G01T 1/1642* (2013.01); *G21K 1/10* (2013.01)

(58) Field of Classification Search
CPC .......... G21K 1/025; G21K 1/10; A61B 6/037; G01T 1/1642
See application file for complete search history.

(56) References Cited

U.S. PATENT DOCUMENTS 6,175,116 B1 1/2001 Gagnon et al.
6,271,524 B1 8/2001 Wainer et al.
(Continued)

FOREIGN PATENT DOCUMENTS

WO 2015097690 A1 7/2015

OTHER PUBLICATIONS

Radiology Key, Performance Parameters of Gamma Cameras, posted Aug. 27, 2016, 6 sheets.
(Continued)

*Primary Examiner* — Kiho Kim
(74) *Attorney, Agent, or Firm* — Daugherty & Del Zoppo, Co. LPA

(57) ABSTRACT

A SPECT imaging system includes a detector unit configured to receive photons emitted by a radiopharmaceutical and convert the photons to projection data. The radiopharmaceutical emits radiation in a higher energy radiation range of interest and a lower energy radiation range of interest, and the detector unit concurrently detects the radiation in the higher and lower energy radiation ranges. The SPECT imaging system further includes a higher energy radiation collimator is positioned between the detector unit and the photons emitted by a radiopharmaceutical. The higher energy radiation collimator is configured for septa penetration for the higher energy radiation of interest without compromising a spatial resolution for the lower energy radiation of interest. The SPECT imaging system further includes a reconstructor configured to reconstruct a first image from projection data for the higher energy radiation of interest and a second image from projection data for the lower energy radiation of interest.

20 Claims, 11 Drawing Sheets

(51) Int. Cl.
*G01T 1/164* (2006.01)
*G21K 1/10* (2006.01)

(56) References Cited

U.S. PATENT DOCUMENTS

| | | | | |
|---|---|---|---|---|
| 9,983,320 | B1 | 5/2018 | Shahar et al. | |
| 10,145,964 | B1 | 12/2018 | Shahar | |
| 10,371,830 | B2 | 8/2019 | Jacobs et al. | |
| 10,617,369 | B2 | 4/2020 | Du | |
| 11,285,663 | B2 | 3/2022 | Bouhnik et al. | |
| 2009/0022279 | A1* | 1/2009 | Wieczorek | A61B 6/4291 378/154 |
| 2012/0085942 | A1 | 4/2012 | Birman et al. | |
| 2013/0272505 | A1* | 10/2013 | Beck | G21K 1/10 29/469 |
| 2023/0146608 | A1 | 5/2023 | Bouhnik et al. | |
| 2023/0389882 | A1 | 12/2023 | Mu | |
| 2024/0008829 | A1 | 1/2024 | Shtern et al. | |

OTHER PUBLICATIONS

Astronuclphysics, Radionuclide scintigraphy—gamma—ray imaging of a radioindicator in nuclear medicine, downloaded Apr. 2024, 119 sheets.

* cited by examiner

IMAGING SYSTEM COLLIMATOR FOR HIGH ENERGY AND LOW ENERGY ISOTOPES

FIELD

The following generally relates to Nuclear Medicine (NM), and more particularly to single photon emission computed tomography (SPECT), and finds particular application with a detector collimator for concurrent acquisition of both high energy and low energy radiation without significantly compromising a spatial resolution for the lower energy radiation or compromising septa penetration for the higher energy radiation.

BACKGROUND

Single photon emission computed tomography (SPECT) imaging provides a non-invasive approach to collect functional information at the molecular and cellular level. In one example, a SPECT imaging system includes a plurality of detectors that are distributed about a rotating frame that is configured to rotate around a patient positioned in an examination region, detect photons emitted by a radiopharmaceutical administered to a patient in a region of interest of the patient over a plurality of angles and output a signal indicative of the detected radiation (projection data), a detector collimator with septa that are spatially arranged with respect to each other (e.g., parallel, converging, diverging, pinhole, etc.) to provide channels in certain directions that pass radiation, allowing it to reach the plurality of detectors, while absorbing other radiation, and a reconstructor that reconstructs the projection data to generate a two-dimensional (2-D) and/or three-dimensional (3-D) imaging data of biological activity in a region of interest of the patient.

In Nuclear Medicine (NM), different applications use different tracers, which emit radiation with different energies. A collimator configured for higher energy radiation applications (a higher energy collimator) is optimized for higher energy applications, e.g., it includes thicker and/or taller septa to limit penetration to higher energy radiation. A collimator configured for lower energy radiation applications (a lower energy collimator) is optimized for lower energy applications, e.g., it includes thinner and/or shorter septa that permit penetration of lower energy radiation to maintain performance of the collimator without degrading the sensitivity of the collimator (geometric efficiency. As such, depending on the application, i.e., low energy (e.g., 40-200 keV) or high energy (e.g., 80-400 keV), a different collimator is utilized (e.g. a collimator with a 40-200 keV range for low energy, a collimator with a 40-500 keV range for high energy). In one instance, e.g., the collimator is manually replaced by an operator, and, in another instance, the detector assembly includes both a lower energy collimator and a higher energy collimator, and the system is configured to switch between the lower and higher energy collimators, depending on the application, using the lower energy collimator for lower energy applications and the higher energy collimator for higher energy applications.

In some instances, a tracer includes multiple energy peaks, e.g., both lower and higher energy radiation energy peaks, emitted from the same isotope, and the prescribed imaging order and/or imaging protocol includes acquiring data for both the lower and higher energy radiation energy peaks. For example, radiotracers such as Actinium-225 (Ac-225) or Astatine-211 (At-211), both for treatment, are alpha-emitting radionuclides that have lower energy gamma rays and higher energy gamma rays used for imaging. Existing lower energy collimators do not limit penetration of higher energy radiation, and existing higher energy collimators usually considerably degrade the spatial resolution for the lower energy radiation. As such, the same collimator is not used for both the lower energy radiation and the higher energy radiation, and the collimator is switched between the lower energy collimator and the higher energy collimator to acquire data for both the lower energy gamma rays and the higher energy gamma rays.

In view of at least the foregoing, there is an unresolved need for an improved approach for multiple energy peak applications.

SUMMARY

Aspects of the application address the above matters, and others. This summary introduces concepts that are described in more detail in the detailed description. It should not be used to identify essential features of the claimed subject matter, nor to limit the scope of the claimed subject matter.

In one aspect, a single photon emission tomography (SPECT) imaging system includes a detector unit configured to receive photons emitted by a radiopharmaceutical and convert the received photons to projection data. The radiopharmaceutical emits radiation in a higher energy radiation range of interest and a lower energy radiation range of interest, and the detector unit concurrently detects the radiation in the higher and lower energy radiation ranges. The SPECT imaging system further includes a higher energy radiation collimator is positioned between the detector unit and the photons emitted by a radiopharmaceutical. The higher energy radiation collimator is configured for septa penetration for the higher energy radiation of interest without compromising a spatial resolution for the lower energy radiation of interest. The SPECT imaging system further includes a reconstructor configured to reconstruct a first image from projection data for the higher energy radiation of interest and a second image from projection data for the lower energy radiation of interest.

In one aspect, a computer-implemented method includes positioning a higher energy radiation collimator of a detector assembly that includes both the higher energy radiation collimator and a lower energy radiation collimator between a radiation detector of the detector assembly and an imaging examination region for an imaging protocol that includes both higher and lower energy radiation. The computer-implemented method further includes acquiring both radiation in a higher energy radiation range of interest and a lower energy radiation range of interest emitted by a radiopharmaceutical in the imaging examination region. The computer-implemented method further includes reconstructing a first image from the higher energy radiation of interest and a second image from the lower energy radiation of interest.

In another aspect, a computer readable medium is encoded with computer executable instructions. The computer executable instructions, when executed by a processor, cause the processor position a higher energy radiation collimator of a detector assembly that includes both the higher energy radiation collimator and a lower energy radiation collimator between a detector unit of the detector assembly and an imaging examination region for an imaging protocol that includes both higher and lower energy radiation, acquire both radiation in a higher energy radiation range of interest and a lower energy radiation range of interest emitted by a radiopharmaceutical in the imaging examination region, and reconstruct a first image from the higher energy radiation of interest and a second image from the lower energy radiation of interest.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings in which like references indicate similar elements.

DETAILED DESCRIPTION

Figure 1:
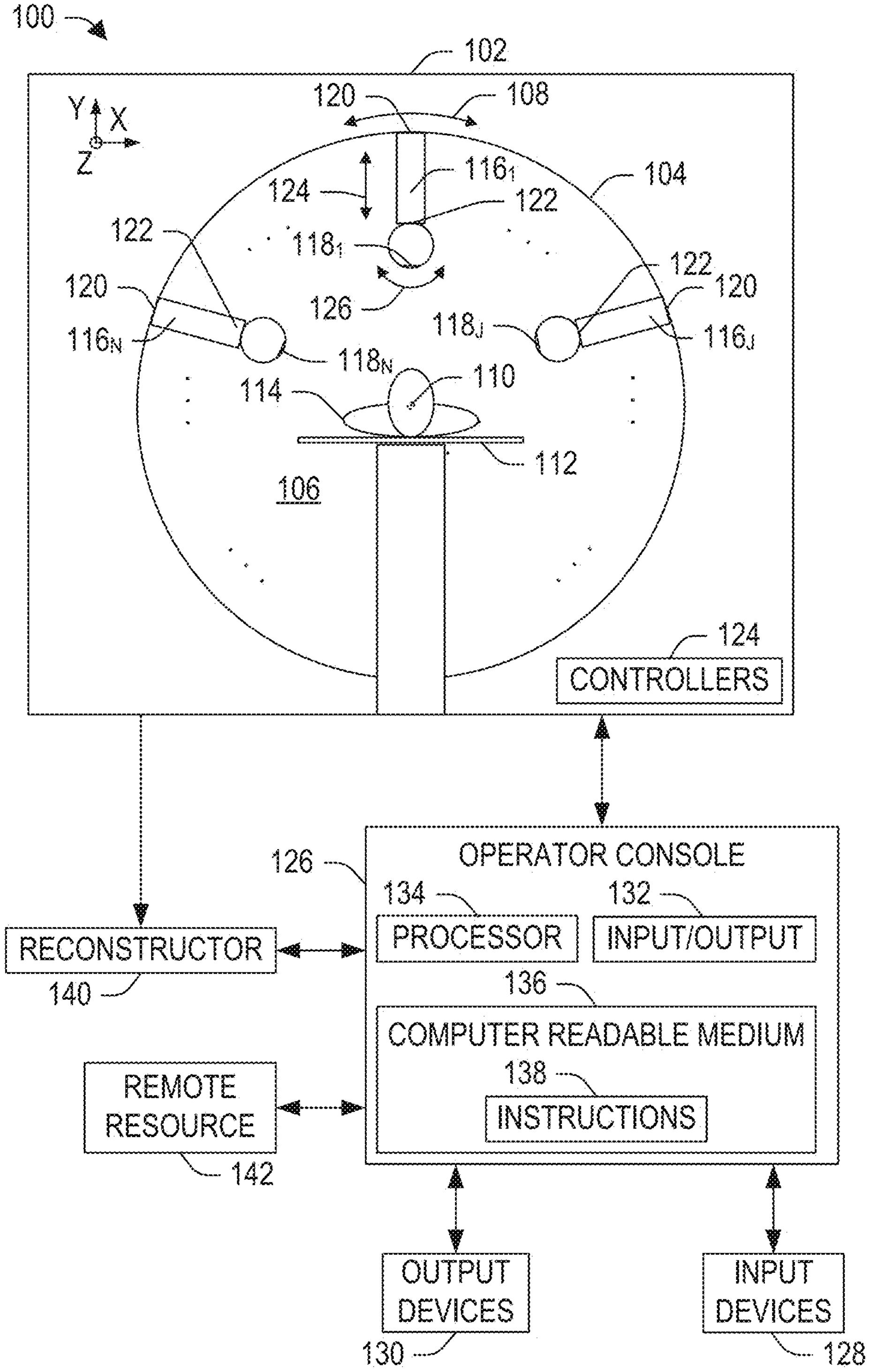
FIG. 1 schematically illustrates a non-limiting example of an imaging system configured for SPECT imaging that includes a detector assembly with both a lower energy collimator and a higher energy collimator where the higher energy collimator is configured for multi-applications, in accordance with an aspect of an embodiment(s) herein.

Embodiments of the present disclosure will now be described, by way of example, with reference to the figures, in which a system, a method and/or instructions of a computer readable medium include employing a collimator configured for higher energy radiation applications (a higher energy collimator) for multi-energy applications where both higher and lower energy radiation is concurrently acquired. In one instance, the higher energy collimator is part of a detector assembly that further includes a detector array and another collimator configured for lower energy radiation applications (a lower energy collimator) where the higher energy collimator and the lower energy collimator are disposed on opposing sides of the detector array and the detector assembly is configured to rotate the collimators to alternatively position one of the collimators in the path of radiation, depending on the application.

By way of non-limiting example, the detector assembly positions the lower energy collimator in the path of radiation for lower energy radiation applications and the higher energy collimator in the path of radiation for higher energy radiation applications and for multi-energy (both lower and higher) radiation applications. As previously discussed, with existing imaging systems the collimator is switched between a lower energy collimator and a higher energy collimator to acquire data for both lower energy applications and higher energy applications. The approach described herein mitigates having to switch between collimators using a single higher energy collimator to concurrently acquire higher energy radiation and lower energy radiation, without significantly compromising a spatial resolution for the lower energy radiation or compromising septa penetration for the higher energy radiation. By concurrently detecting lower and higher energy radiation, image acquisition time can be reduced relative to switching between collimators for the lower and higher energy radiation acquisitions.

As described in greater detail below, in one instance the septa configuration of the higher energy radiation collimator and the septa configuration of the lower energy radiation collimator are such that the collimators have a substantially similar aspect ratio. As such, the higher energy radiation collimator will provide a spatial resolution for lower energy radiation applications that is comparable to the spatial resolution for lower energy radiation applications using the lower energy radiation collimator. In addition, the septa can be variously arranged with respect to each other and/or variously shaped where parameters (e.g., height, width, pitch, etc.) for the different shaped septa can be the same or configured to match a sensitivity or a resolution between the different shapes. In another instance, the higher energy radiation collimator is part of a radiation detector assembly that includes only a single collimator and can be used for higher energy applications, lower energy applications, or mixed (higher and lower)-energy applications.

FIG. 1 schematically illustrates an example of an imaging system 100 configured for a Nuclear Medicine (NM) application such as single photon emission computed tomography (SPECT) imaging. The imaging system 100 includes a gantry 102 and a frame 104. In one instance, the frame 104 includes an annular ring with an inner material free region (a bore, an aperture, an opening, etc.) that serves as an examination region 106, is rotatably supported by the gantry 102, e.g., via a bearing or the like, and is configured to rotate 108 around the examination region 106 about a "z" or rotational axis 110. In other instances, the gantry 102 is otherwise shaped such as "C," "H," "L," etc.

The imaging system 100 further includes a subject/object support 112 configured to support a subject/object 114 before, during and/or after an imaging examination. The subject/object support 112, as illustrated, is configured to support a lying subject, where the subject/object 114 is loaded onto the subject/object support 112, the subject/object support 112 is moved into the examination region 106 such that a center of the subject/object 114 in an axial direction approximately aligns with the "z" or rotational axis 110, an imaging examination is performed, and the subject/object support 112 is moved out of the examination region 106 to unload the subject/object 114. In some instances, the subject/object support 112 is configured to support a standing, a sitting, a leaning and/or otherwise positioned subject.

The imaging system 100 further includes N elongate support arms $\mathbf{116}_1, \ldots, \mathbf{116}_J, \ldots, \mathbf{116}_N$ and N radiation detectors $\mathbf{118}_1, \ldots, \mathbf{118}_J, \ldots, \mathbf{118}_N$, where N is an integer equal to or greater than one. For example, a single head or a dual head camera may be used. Alternatively, and optionally, N may be greater than 5, for example N=12. Collectively, the N support arms $\mathbf{116}_1, \ldots, \mathbf{116}_J, \ldots, \mathbf{116}_N$ are referred to herein as support arms 116, and the N radiation detectors $\mathbf{118}_1, \ldots, \mathbf{118}_J, \ldots, \mathbf{118}_N$ are referred to herein as radiation detectors 118. The support arms 116 include first ends 120 and second ends 122, which spatially oppose the first ends 120. The first ends 120 are supported at the frame 104 and are angularly spaced apart from each other around the frame 104. The second ends 122 support the radiation detectors 118. The support arms 116 and radiation detectors 118 rotate in coordination with the rotating frame 104 about the "z" or rotational axis 110.

The support arms 116 are each configured to extend and retract radially 124 between the frame 104 and the axis of rotation 110, where extending a support arm 116 moves the respective radiation detector 118 towards and closer to the axis of rotation 110 and hence the subject/object 114 and retracting a support arm 116 moves the respective radiation detector 118 away from the axis of rotation 110 and hence the subject/object 114. In some optional embodiments, at least few of arms 116 moves the respective radiation detector 118 towards and closer to the subject/object 114 in trajectories that are parallel to each other, instead of radial motion towards the axis of rotation 110. In some other optional embodiments, at least few of arms 116 are connected to frame 104 with articulate joint that can change the direction of the motion of arms 116 relative to the axis of rotation 110. Such movement can be provided via an actuator such as an actuator that converts rotary motion into linear displacement, an actuator with a hollow cylinder and a piston, and/or the like, before, during and/or after an imaging examination.

The radiation detectors 118 are moveably affixed to the second ends 122 of the support arms 116. In one instance, the radiation detectors 118 are configured to swivel 126 (sweep, pivot, rotate, etc. in one or more axis directions) at the second ends 122 of the support arms 116. The movement of the radiation detectors 118 can be independently controlled such that one or more of the radiation detectors 118 can, e.g., swivel, while one or more other radiation detectors 118 remains stationary. The one or more of the radiation detectors 118 can be moved in coordination with each other and/or otherwise. Swiveling a radiation detector 118 focuses a detection surface of the radiation detector 118 in the examination region 106 along particular paths of radiation from the subject/object 114, e.g., along a specific portion or organ of the subject/object 114.

In one instance, each of the radiation detectors 118 at least includes one or more modules or tiles (not visible), each including an array of one or more radiation sensitive pixels (not visible), two collimators (not visible) and electronics (not visible). In one instance, the one or more arrays of radiation pixels include a direct conversion material such as Cadmium Zinc Telluride (CZT), Cadmium Telluride (CdTe), etc., the collimators include material free channels that allow radiation to pass unobstructed and septa therebetween configured to absorb and attenuate radiation impinging thereon, and the electronics (not visible) route electrical signals indicative of detected radiation off the radiation detector 118. In general, incident gamma rays deposit their energy in the pixel crystal lattice generating pairs of charge carriers, an applied electric field collects the charge carriers to produce a current pulse, and, since the current pulse comes from a single pixel, its position is known.

In another example, the one or more arrays of radiation pixels include an indirect conversion material such as a thallium-doped sodium iodide (NaI(TI)) scintillation crystal that converts X-ray, gamma ray, etc. radiation to light photons, the collimators include material free channels that allow light photons to pass unobstructed and septa therebetween configured to absorb and attenuate light photons impinging thereon, and the electronics (not visible) include photomultiplier tubes (PMTs) that convert the light photons into electrical signals indicative of an energy of the photons. In another instance, the indirect conversion material includes a pixelated NaI(TI) scintillation crystal that converts X-ray, gamma ray, etc. radiation to light photons and the electronics includes PMTs or a solid-state photodiode (PD) array that convert the light photons into electrical signals indicative of an energy of the photons.

Figure 2:
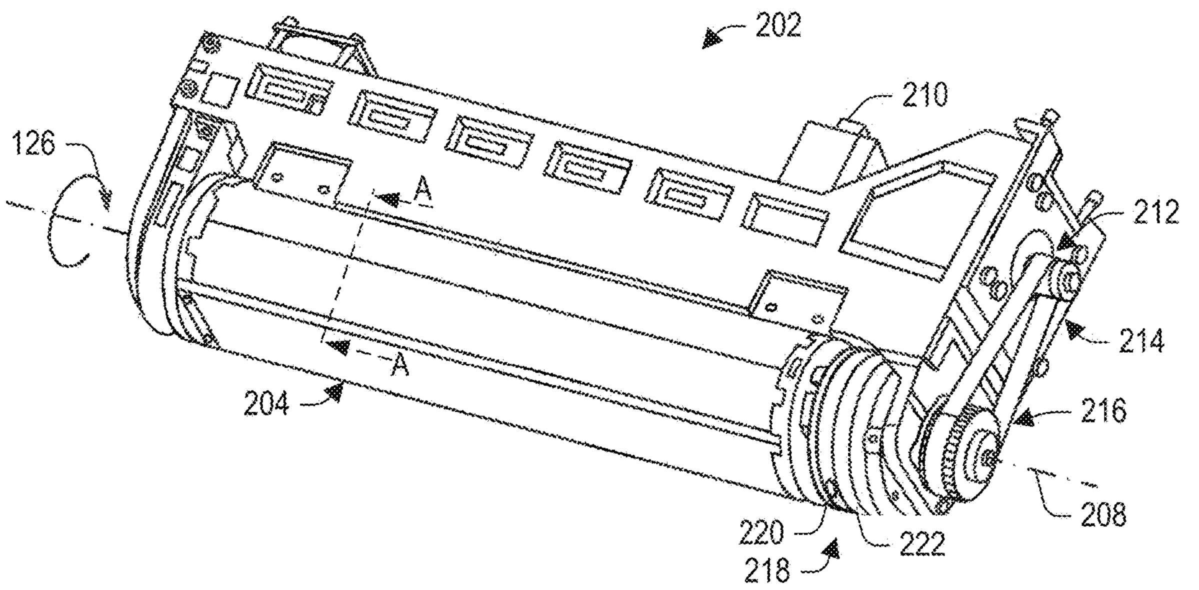
FIG. 2 schematically illustrates a perspective view of a non-limiting example of the detector assembly of the imaging system, in accordance with an aspect of an embodiment(s) herein.

Initially referring to FIG. 2, an example of a radiation detector assembly 202 includes a detector unit 204 and a pivoting and supporting mechanism 206. The pivoting and supporting mechanism 206 has a long axis 208. Relative to FIG. 1, the long axis 208 is aligned in a direction of the "z" or rotational axis 110. The detector unit 204 is rotatably mounted in the radiation detector assembly 202 to rotate about the long axis 208. The pivoting and supporting mechanism 206 further includes a motor 210 and a drive system 212. The motor 210 is coupled to a first side 214 of the drive system 212, and the detector unit 204 is coupled to a second, opposing side 216 of the drive system 212. The motor 210 is configured to rotate the first side 214 of the drive system 212, which rotates the second, opposing side 216 of the drive system 212, thereby rotating the detector unit 204. The radiation detector assembly 202 further includes a slip ring 218 configured for transferring signals between the detector unit 204 and non-rotating electronics of the radiation detector assembly 202. A first side 220 of the slip ring 218 is attached to the detector unit 204, and a second side 222 of the slip ring is attached to the radiation detector assembly 202. In some embodiments, the slip-ring 218 is a wireless NFC (Near Field Communication) device for signal transfer, or with a spiral cable as disclosed in U.S. Pat. No. 9,689,720.

Figure 3:
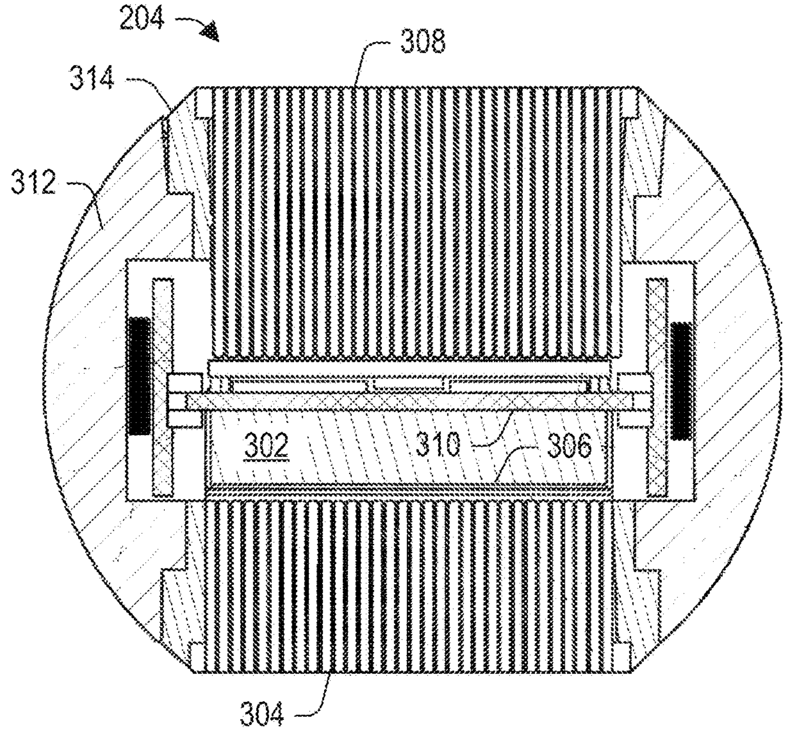
FIG. 3 schematically illustrates a cross-sectional view of a portion of the non-limiting example of the detector assembly of the imaging system, in accordance with an aspect of an embodiment(s) herein.

Moving to FIG. 3, a cross-sectional view of a portion of the column 204 along line A-A of FIG. 2 is illustrated. The portion includes a semiconductor crystal 302, the portion further includes a first collimator 304 disposed on a first side 306 of the semiconductor crystal 302, a second collimator 308 disposed on a second, opposing side 310 of the semiconductor crystal 302, a shielding 312, and an optional collimator fame 314. The first collimator 304 is configured for utilization during an imaging scan involving radiation in a lower energy range. The second collimator 308 is configured for utilization during an imaging scan involving radiation in a higher energy range.

Figure 4:
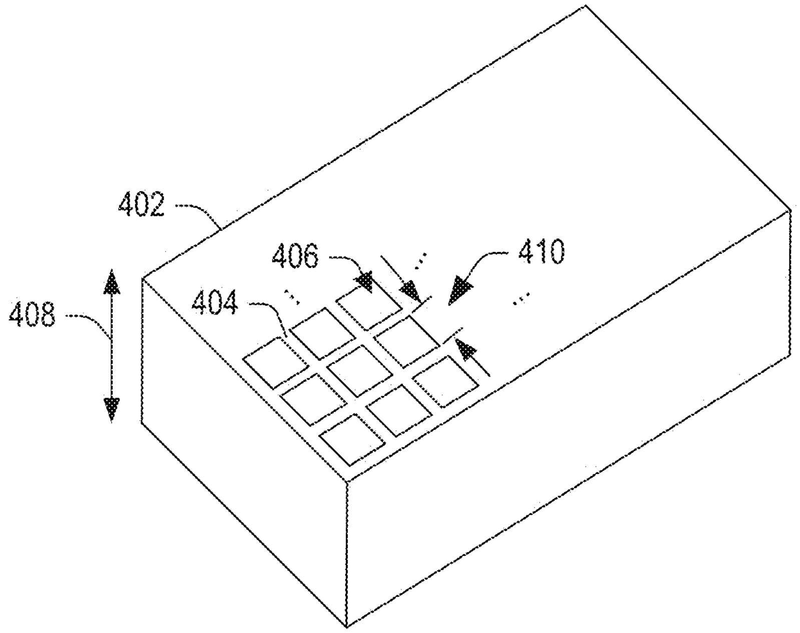
FIG. 4 schematically illustrates a perspective view of a non-limiting example of a detector collimator, in accordance with an aspect of an embodiment(s) herein.

FIG. 4 schematically illustrates a non-limiting example of a detector collimator 402 (e.g., the collimator 304 and/or the collimator 308). The detector collimator 402 includes septa 404 that absorbs radiation and apertures 406 that allow radiation to pass through the detector collimator 402. The septa have a height 408 and a width 410, and a pitch (i.e., spacing between) that defines the apertures 406.

Figure 5:
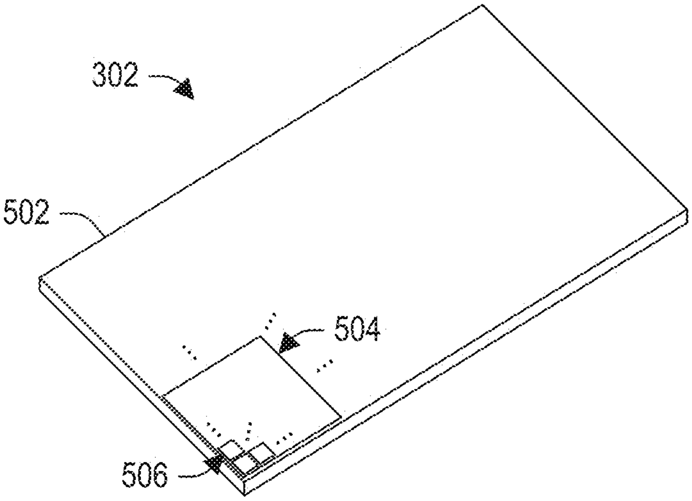
FIG. 5 schematically illustrates a perspective view of a non-limiting example of a radiation detector that includes one or more detector modules, each of the detector modules including one or more detector pixels, in accordance with an aspect of an embodiment(s) herein.

FIG. 5 schematically illustrates the radiation detector 302 as including a substrate 502 with one or more modules 504, which include a pixelated module with one or more pixels 506. An example of the radiation detector 302 includes a 1×7 array of modules 504, each of the modules 502 is approximately 40×40 millimeters (40 $mm^2$) and including a 40×40 array of approximately 1.0×1.0 mm (1.0 $mm^2$) detector pixels, for a total of 160 pixels per module 504, and 11,200 detector pixels per radiation detector 302. Other numbers and/or sizes of modules and/or pixels are contemplated herein. In addition, FIG. 5 shows a rectangular substrate 502 and square modules 504 and pixels 506, and other shaped substrates 502, modules 504 and pixels 506 are contemplated herein.

With reference to FIGS. 2-5, the column 204 is configured to rotate about the long axis 206 to position either the first collimator 304 or the second collimator 308 to face the subject/object support 112 (FIG. 1) for use during an imaging scan. In general, the column 204 can be rotated more than one hundred and eighty degrees (±180°), e.g., three-hundred and sixty degrees (±360°), four-hundred and eighty degrees (±480°), etc. to switch between the first and second collimators 304 and 308 and may be rotated (e.g., approximately one hundred and five degrees, or ±105 degrees) during a scan to swivel and focus the first and second collimators 304 and 308 with respect to the subject/object 114.

As discussed in greater detail below, the higher energy radiation collimator 308 is configured for higher energy radiation applications, and can also be utilized for multi-energy applications where the high energy collimator 308 simultaneously and/or concurrently detects higher energy radiation and lower energy radiation and is configured to preserve a same aspect ratio as the lower energy collimator 304, permitting to acquire low energy radiation with the high energy collimator 308, with approximately the same spatial resolution as for the low energy collimator 304 and without compromising septa penetration for the high energy radiation.

Returning to FIG. 1, the imaging system 102 further includes one or more controllers 124. In one instance, the controllers 124 include one or more of a gantry rotation controller, a subject support controller, a radial arm motion controller, a detector pivoting controller, and a scanning controller. In one instance, the controllers are automatically controlled by the imaging system 102, manually controlled by an operator, or a combination thereof. The gantry controller is configured to move the radiation detectors 118 with respect to the subject/object 114, e.g., individually, in segments or subsets, or simultaneously in a fixed relationship to one another. For example, in some embodiments, the gantry controller may cause the radiation detectors 118 and/or arms 116 to rotate about the "z" or rotational axis 110.

The subject support controller is configured to move the subject/object support to position the subject/object 114 relative to the radiation detectors 118, including up-down, in-out directions, right-left directions. The radiation detector controller is configured to control movement of each of the radiation detectors 118 to move together as a group or individually. In some embodiments, the radiation detector controller is further configured to control movement of the radiation detectors 118 to move closer to and farther from a surface of the subject/object 114, such as by controlling translating movement of the arms 116 linearly towards or away from the subject/object 114 (e.g., sliding or telescoping movement).

The scanning controller is configured to rotate the detector column 204 (FIG. 2) of a radiation detector 118 between the collimator 304 and the collimator 308 (FIG. 3), depending on the radiation energy of interest for a scan (lower, higher or both lower and higher). In one instance, the collimator controller aligns the collimator 308 configured for higher energy radiation for a multi-energy application where both higher energy radiation and lower energy radiation are currently being detected. The swivel controller is configured to control swiveling or rotating movement of the radiation detectors 118. For example, one or more of the radiation detectors 118 may be rotated to view the subject/object 114 from a plurality of different angular orientations to acquire, e.g., 3-D image data.

The imaging system 102 further includes a computing system 126, e.g., a computer, a workstation, a server, or the like, which serves as an operator console. The operating console 126 includes one or more input devices 128 such as a keyboard, mouse, touchscreen, microphone, etc., one or more output devices 130 includes a human readable device such as a display monitor or the like, and input/output (I/O) 132 for sending and/or receiving signals and/or data. The operator console 126 further includes one or more processors 134 such as a microprocessor (μP), a central processing unit (CPU), a graphics processing unit (GPU), etc., and a computer readable medium 136, which includes non-transitory medium and excludes transitory medium (signals, carrier waves, and the like).

The computer readable medium 136 is embedded or encoded with instructions 138. The processor(s) 134 is configured to execute at least one of the instructions 138. The instructions 138, in one instance, includes application software for presenting a user interface for planning and/or scanning subjects or objects. The instructions 138 include instructions, e.g., for controlling the collimator controller, which controls which collimator (i.e., the first collimator 304 or the second collimator 308) faces the subject/object 114 for a scan, the rotation of the frame 104 and hence the radiation detectors 118 during a scan, and the radial position 124 of the radiation detectors 118 and the swiveling 126 of the radiation detectors 118 during a scan, etc.

A reconstructor 140 reconstructs the projection data. Suitable reconstruction algorithms include a filtered back-projection algorithm, an iterative algorithm, etc. The reconstructor 140 reconstructs a 2-D axial slice(s) and/or 3-D volumetric imaging data. The 2-D axial slice(s) and/or 3-D volumetric imaging data can be visually presented via a display monitor of the one or more output devices 130, optionally printed, transferred to a cloud resource, a server, a workstation, a Radiology Information System (RIS), a Hospital Information System (HIS), an electronic medical record (EMR), and/or a Picture Archiving and Communications System (PACS), etc.

The imaging system 100 is in electrical communication with a remote resource 142. In one instance, the remote resource 142 includes one or more of a server, a workstation, a RIS, a HIS, an EMR, a PACS, one or more other scanners, cloud processing resources (which includes shared remote data storage and/or computing power, including processing resources distributed over multiple locations/data centers), etc. The remote resource 142 is in communication with the computing system 126 through the I/O 132 and/or otherwise. Images can be transferred therebetween and stored via Digital Imaging and Communications in Medicine (DICOM), etc., and other data can be transferred via Health Level Seven (HL7), etc.

Figure 6:
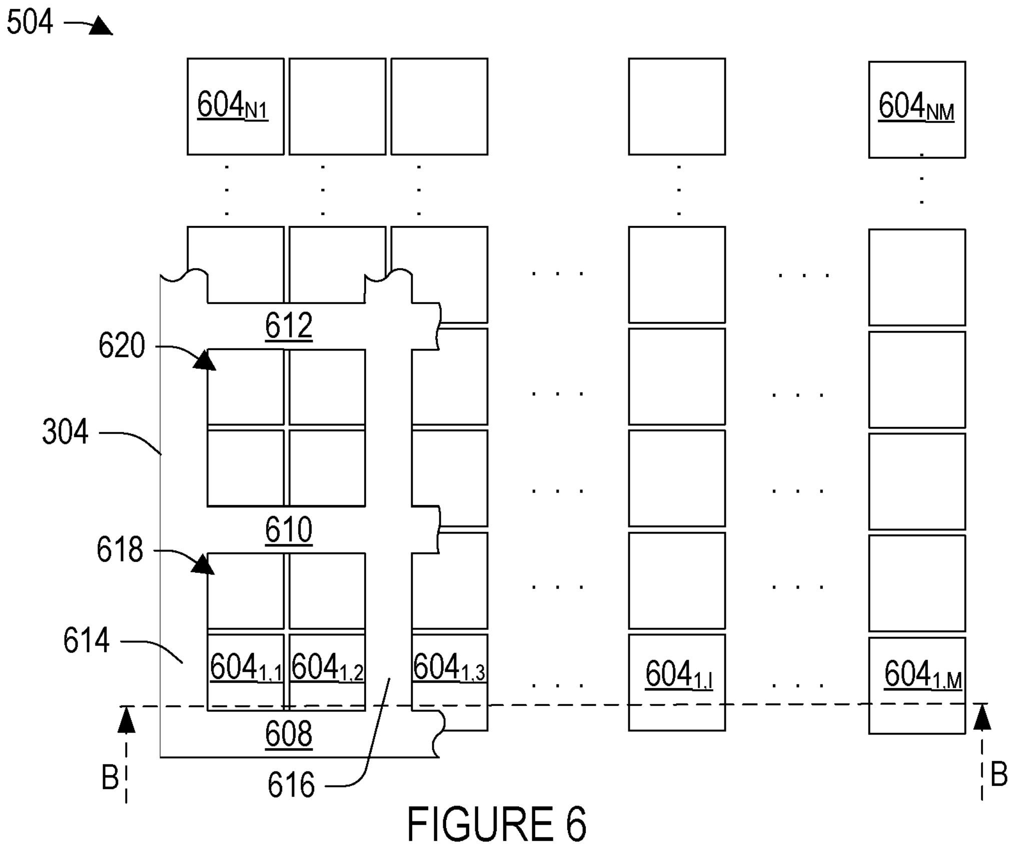
FIG. 6 schematically illustrates a top-down view of a sub-portion of the radiation detector with a sub-portion of a lower energy radiation collimator, in accordance with an aspect of an embodiment(s) herein.
Figure 7:
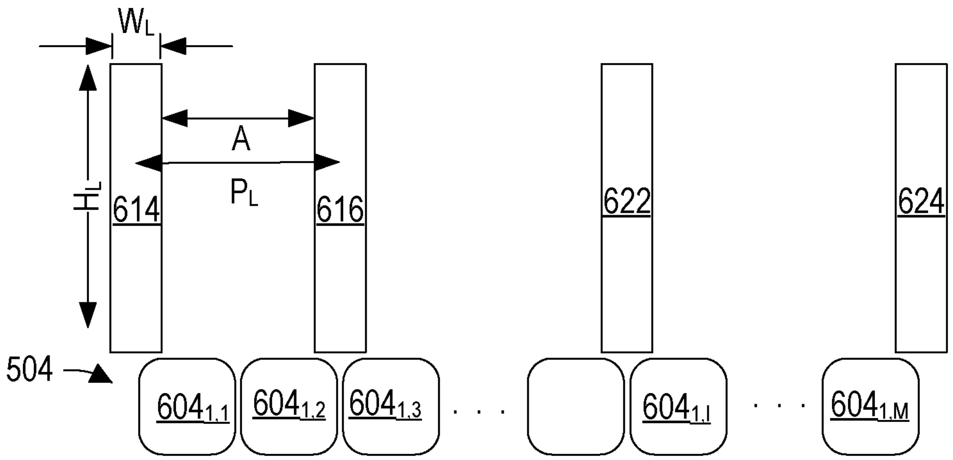
FIG. 7 schematically illustrates a cross-sectional view of the example in FIG. 6, in accordance with an aspect of an embodiment(s) herein.
Figure 8:
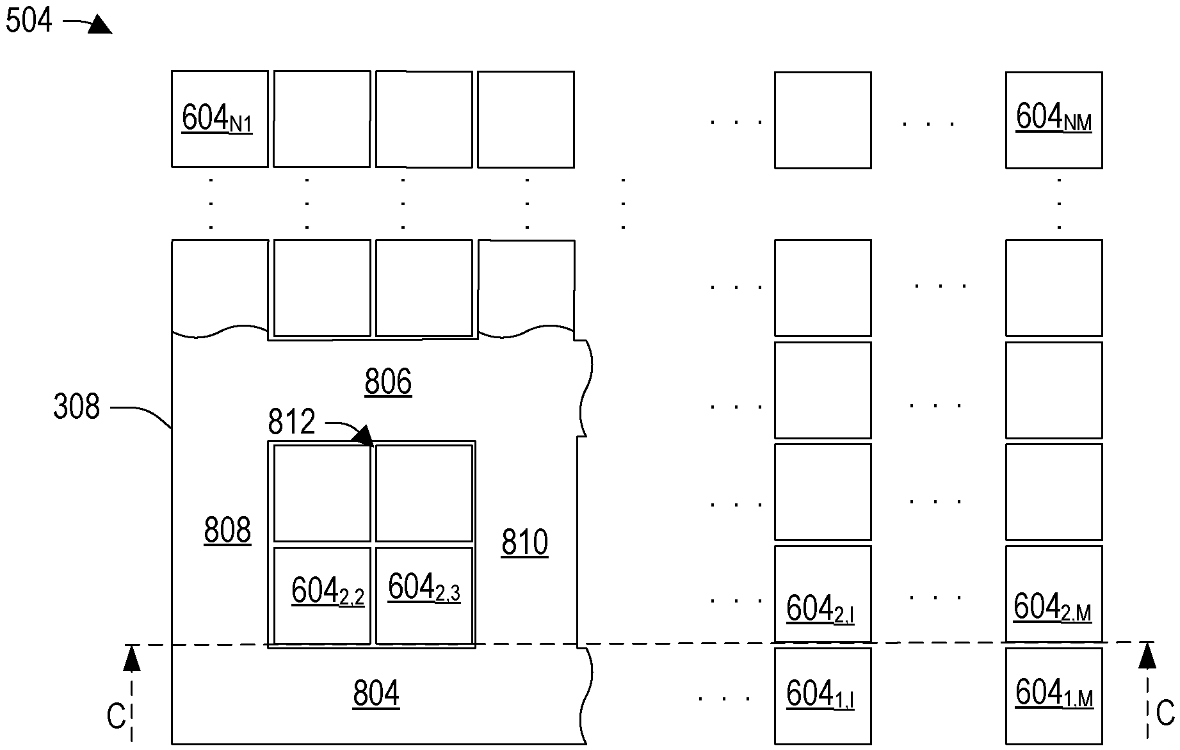
FIG. 8 schematically illustrates a top-down view of a sub-portion of the radiation detector with a sub-portion of a higher energy radiation collimator, in accordance with an aspect of an embodiment(s) herein.
Figure 9:
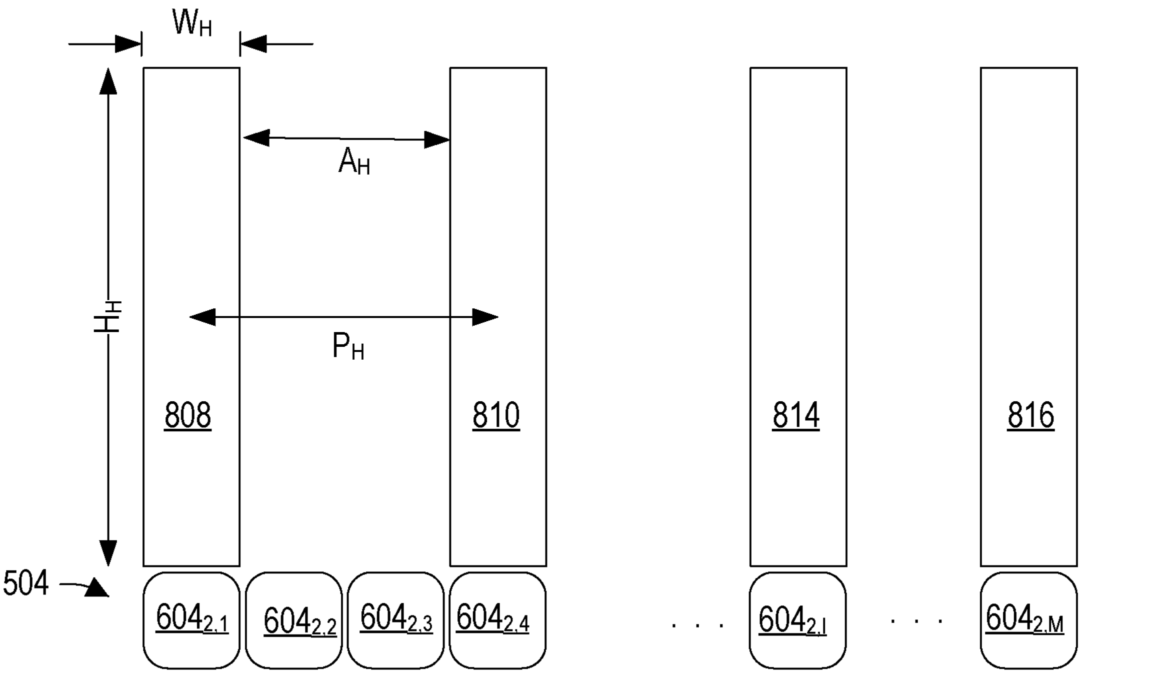
FIG. 9 schematically illustrates a cross-sectional view of the example in FIG. 8, in accordance with an aspect of an embodiment(s) herein.

FIGS. 6, 7, 8 and 9 schematically illustrate examples of the lower energy radiation collimator 304 and the higher energy radiation collimator 308, which is configured for higher energy radiation applications and is utilized for multi-energy (both higher and lower energy radiation) applications. FIGS. 6 and 7 schematically illustrate an example of the lower energy radiation collimator 304, and FIGS. 8 and 9 schematically illustrate the higher energy radiation collimator 308. In FIGS. 6, 7, 8 and 9, sizes and/or shapes of components is for clarity and explanatory purpose, and may or may not reflect actual component size and/or shape.

Beginning with FIGS. 6 and 7, FIG. 6 schematically illustrates a top-down view of a portion of the module 504 (FIG. 5) of the radiation detector 302 (FIG. 3) with a sub-portion of the collimator 402 (FIG. 4), which is the lower energy radiation collimator 304 in this example. The detector module 506 includes pixels $\mathbf{604}_{1,1}$, $\mathbf{604}_{1,2}$, $\mathbf{604}_{1,3}$, . . . , $\mathbf{604}_{1,J}$, $\mathbf{604}_{1,M}$, . . . , $\mathbf{604}_{N,1}$, . . . , and $\mathbf{604}_{N,M}$, where N and M are positive integers. The illustrated sub-portion of the lower energy radiation collimator 304 includes septa 608, 610, 612, and perpendicularly oriented septa 614, 616, etc., which are spatially separated from each other, forming square apertures 618 and 620, etc.

FIG. 7 schematically illustrates a cross-sectional side view along a line B-B in FIG. 6. FIG. 7 additionally shows septa 622 and 624.

In the illustrated example, the septa 608, 610, 612, 614, 616, 622 and 624 have a height ($H_L$) and a width ($W_L$) and are aligned with respect to gaps between the detector pixels 506 with a pitch ($P_L$) corresponding to a center-to-center distance, which defines a dimension ($A_L$) of the square apertures 618 and 620. By way of non-limiting example, in one instance $H_L$=19 mm, $W_L$=0.426 mm, and $P_L$=2 detector pixels in both N and M directions. Where the radiation detector 302 includes an array of seven (7) modules 504, each approximately 40×40 mm, and each detector pixel is approximately 0.984 $mm^2$, the lower energy radiation collimator 304 will include 20×140 apertures, each being approximately 1.56×1.56 mm (1.56 $mm^2$). With this configuration, the aspect ratio (AR) is $AR_L$=aperture length divided by septa height=1.56 mm/19 mm=0.082. In an exemplary embodiment, there are 10×10 (or 20×20, 40×40, etc.) pixels in each module, and the pitch of the pixels (Pp) is 1×1 mm. The pitch of the collimators ($P_L$) is $K_L$*Pp, wherein $K_L$ is an integer (2 in this depicted example), thus the collimators are "registered" to the pixels.

Next with FIGS. 8 and 9, FIG. 8 schematically illustrates the top-down view of a portion of the module 504 (FIG. 5) of the radiation detector 302 (FIG. 3) with a sub-portion of the collimator 402 (FIG. 4), which is the higher energy radiation collimator 308 in this example. The detector module 506 includes pixels $\mathbf{604}_{1,1}$, . . . , $\mathbf{604}_{1,M}$, . . . , $\mathbf{604}_{2,2}$, $\mathbf{604}_{2,3}$, . . . , $\mathbf{604}_{2,1}$, . . . , $\mathbf{604}_{2,M}$, . . . , $\mathbf{604}_{N,1}$, . . . , and $\mathbf{604}_{N,M}$. The illustrated sub-portion of the higher energy radiation collimator 308 includes septa 804, 806, 808 and 810, which are spatially separated from each other, forming a square aperture 812.

FIG. 9 schematically illustrates a cross-sectional side view along a line C-C in FIG. 8. FIG. 9 additionally shows septa 814 and 816.

In the illustrated example, the septa 804, 806, 808 and 810 have a height ($H_H$) and a width ($W_H$) and are aligned with respect whole detector pixels with a pitch ($P_H$) corresponding to a center-to-center distance, which defines a dimension ($A_H$) of the square aperture 812. By way of non-limiting example, in one instance $H_H$=24 mm, $W_L$=1.0 mm, and $P_L$=3 detector pixels in both N and M directions. Where the radiation detector 302 includes an array of seven (7) modules 504, each approximately 40×40 mm, and each detector pixel is approximately 0.984 $mm^2$, the high energy radiation collimator 308 will include 13×93 apertures, each being approximately 1.95×1.95 mm (1.95 $mm^2$). With this configuration, the aspect ratio (AR) is $AR_H$=aperture length divided by septa height=1.95 mm/24 mm=0.081. In an exemplary embodiment, there are 10×10 pixels in each module, and the pitch of the pixels ($P_p$) is 1×1 mm. The pitch of the collimators ($P_H$) is $K_H$*$P_H$, wherein $K_H$ is an integer (3 in this depicted example). Thus, the collimators are "registered" to the pixels.

Continuing with reference to FIGS. 6, 7, 8 and 9, the $AR_L$ and the $AR_H$ are within 2.5% of each other. As discussed herein, increasing the AR decreases spatial resolution. Since the $AR_H$ and $AR_L$ are approximately equal (e.g., within 10%, 8%, 5%, etc.), the higher energy radiation collimator 308 configured can be used for multi-energy peak applications that concurrently include both higher energy radiation and lower energy radiation, with a spatial resolution for the lower energy radiation similar to a resolution for the lower energy radiation using the lower energy radiation collimator 304. With this configuration, the higher energy radiation collimator 308 satisfies septal penetration requirements without considerably sacrificing the spatial resolution for the lower energy radiation. As such, the imaging system 102 can utilize the higher energy radiation collimator 308 for higher and multi-energy radiation applications, while using the lower energy radiation collimator 304 for lower energy radiation applications, while preserving the high sensitivity needed for the more common lower energy applications.

Variations are contemplated.

The example imaging system 102 described in connection with FIGS. 1-9 included the radiation detector assemblies 118 with both the lower energy radiation collimator 304 configured and the higher energy radiation collimator 308 configured for higher energy radiation applications and which can also be utilized for mixed-energy (both lower and higher) applications. In a variation, the radiation detectors 118 only include the higher energy radiation collimator 308, which is utilized for higher energy radiation applications, multi-energy radiation (both lower and higher) applications, and lower energy radiation applications.

The septa shown in FIGS. 6-9 have planar sides facing the apertures. In a variation, the septa are otherwise shaped. An example variation has a same cross-sectional width at a center of a height of the septa and smaller cross-sectional widths at a top end and/or a bottom end of the height of the septa. In one instance, the cross-sectional width at the top end and the bottom end are equal. In another instance, the cross-sectional width at the top end and the bottom end are not equal.

Figure 10:
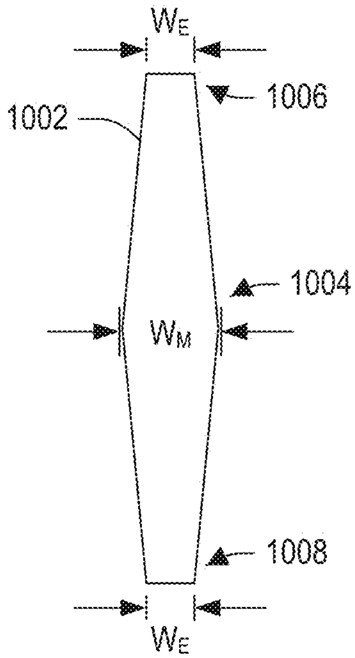
FIG. 10 schematically illustrates a variation of a shape of the septa, in accordance with an aspect of an embodiment(s) herein.

By way of example, FIG. 10 schematically illustrates a variation in which a septum 1002 has a middle width $W_M$ (where $W_M=W_H$) at a cross section 1004 at a middle of the septum 1002 and equal end widths $W_E$ at cross sections 1006 and 1008 at ends of the septum 1002. In this example, the widths of the septum 1002 linearly decrease from $W_M$ to $W_E$, having a thicker middle section. Similar to the configuration described in connection with FIG. 9, with the configuration of the septum 1002, sensitivity is increased at the cost of resolution, and the aspect ratio can be optimized to improve overall performance.

Figure 11:
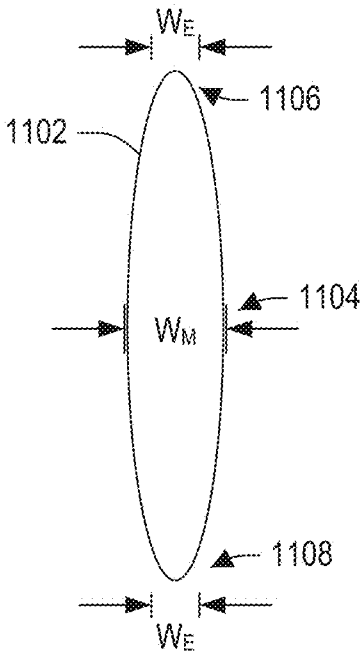
FIG. 11 schematically illustrates yet another variation of a shape of the septa, in accordance with an aspect of an embodiment(s) herein.

FIG. 11 schematically illustrates another variation in which a septum 1102 is ellipsoid shaped and the sides are curved, and not linear like the septum 1002 in FIG. 10. Another variation includes a combination of the septum 1002 of FIG. 10 and the septum 1102 of FIG. 11, e.g., with at least one linear region and at least one curved region. Other shapes are also contemplated herein.

The following provides a performance comparison between the septa in FIGS. 6-9 and the septa based on the septum 1002 in FIG. 10. Where the height, pixel pitch ($p_p$) and center width (W) are equal, and the ends of the septum 1002 in FIG. 10 are smaller than the ends of the septa in FIGS. 6-9 (e.g., $W_E=W_M/2$), the septum 1002 in FIG. 10 increases a sensitivity of the high energy radiation collimator 308 while maintaining low penetration as rays traversing the ends of the septum 1002 traverse at more oblique angles relative to rays traversing the middle of the septum 1002, and, as such the rays traversing the ends of the septum 1002 have a similar length trajectory through the septum 1002 as the rays traversing the middle of the septum 1002. In general, increasing sensitivity may decrease spatial resolution.

To achieve approximately equal spatial resolution, the height of the septum 1002 can be increased. For example, continuing with the above example, where the height of the septum 1002 can be increased from 24 mm to, e.g., 30.5 mm, the spatial resolution of the collimator having a septum 1002 and the collimator seen in FIGS. 6-9 are approximately equal and the sensitivity of the collimator based on the septum 1002 in FIG. 10 increases. To achieve approximately equal sensitivity, the height of the septum 1002 can be increased even further, e.g., from 24 mm to, e.g., 36 mm, and the sensitivity of the septum 1002 and the septa in FIGS. 6-9 is approximately equal and the spatial resolution of the septum 1002 in FIG. 10 increases. In other examples, other parameters can be changed to achieve approximately equal spatial resolution, sensitivity, and/or other metric.

FIGS. 12-15 schematically illustrate other suitable arrangements for the septa described in connection with FIGS. 8 and 9. For explanatory purposes, FIGS. 12-15 are described only along a single row and for M=40 detector pixels, for 1 $mm^2$ pixels' pitch ($P_p$).

In FIGS. 8 and/or 9, the height $H_H$ of the septum 808 is directly aligned with a height of the detector pixel $\mathbf{604}_{2,1}$ height $H_H$ and the width of $W_H$ of the septum 808 is directly aligned with a width of the detector pixel $\mathbf{604}_{2,1}$, the height $H_H$ of the septum 810 is directly aligned with a height of the detector pixel $\mathbf{604}_{2,4}$ height $H_H$ and the width of $W_H$ of the septum 808 is directly aligned with a width of the detector pixel $\mathbf{604}_{2,4}$, the height $H_H$ of the septum 814 is directly aligned with a height of the detector pixel $\mathbf{604}_{2,1}$ and the width of $W_H$ of the septum 808 is directly aligned with a width of the detector pixel $\mathbf{604}_{2,1}$, and the height $H_H$ of the septum 816 is directly aligned with a height of the detector pixel $\mathbf{604}_{1,M}$ and the width of $W_H$ of the septum 808 is directly aligned with a width of the detector pixel $\mathbf{604}_{1,M}$. In general, in this example, widths of the spectra are approximately the same as (i.e., within tolerance of) widths of the detector pixel.

Figure 12:
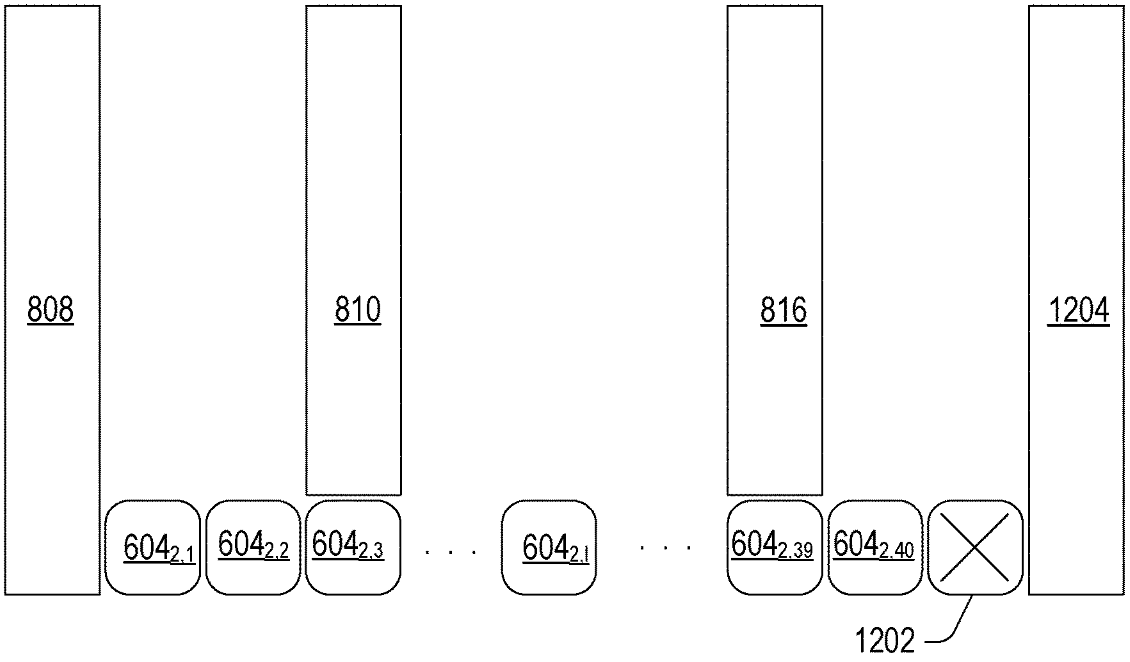
FIG. 12 schematically illustrates another arrangement of the septa for the higher energy radiation collimator with respect to the detector pixels, in accordance with an aspect of an embodiment(s) herein.

Relative to FIGS. 8 and/or 9, in FIG. 12, the septa 808, 810 and 816 are all shifted to the left by one (1) full pixel. The septum 808 is now disposed next to the detector pixel $\mathbf{604}_{2,1}$ along the illustrated row and before the first detector pixel of the row (i.e., before the detector pixel $\mathbf{604}_{2,1}$). The first and last septa are extended by approximately a height of the detector pixels. The septum 810 is now directly aligned with detector pixel $\mathbf{604}_{2,3}$. The first septum 808 and the last septum 1204 are adjacent to the shielding 312 (FIG. 3) and the collimator frame 314 (FIG. 3). The first septum 808 and the last septum 1204 both include radiation opaque materials. In another instance, the first septum 808 and/or the last septum 1204 are part of the collimator frame 314. The septum 814 is now directly aligned with a detector pixel not shown in FIGS. 8 and 9 and thus is not shown in FIG. 12. The septum 816 is now directly aligned with detector pixel $\mathbf{604}_{2,39}$ (the detector pixel to the left of the detector pixel $\mathbf{604}_{2,M}$, i.e., the detector pixel $\mathbf{604}_{2,(M-1)}$).

A space, represented here by an inactive pixel 1202 is added after the last detector pixel $\mathbf{604}_{2,M}$, and a septum 1204 is added next to the inactive pixel 1202, along the illustrated row, and extended by approximately a height of the detector pixels. With this configuration, an additional column of pixels detects radiation. Virtually adding space 1202 is done to create the same viewing angles to active pixel $\mathbf{604}_{1,40}$ as to all other pixels. Thus, the reconstruction algorithm can use the same system matrix to all pixels. This space can be filled with radiation opaque material. When observing a row of single 10-pixels modules, in accordance to FIGS. 9, where the first and last pixels are obscure, only 6 pixels are exposed. In contrast, according to FIG. 12, 7 pixels are exposed, an increased sensitivity of 16.6%.

Figure 13:
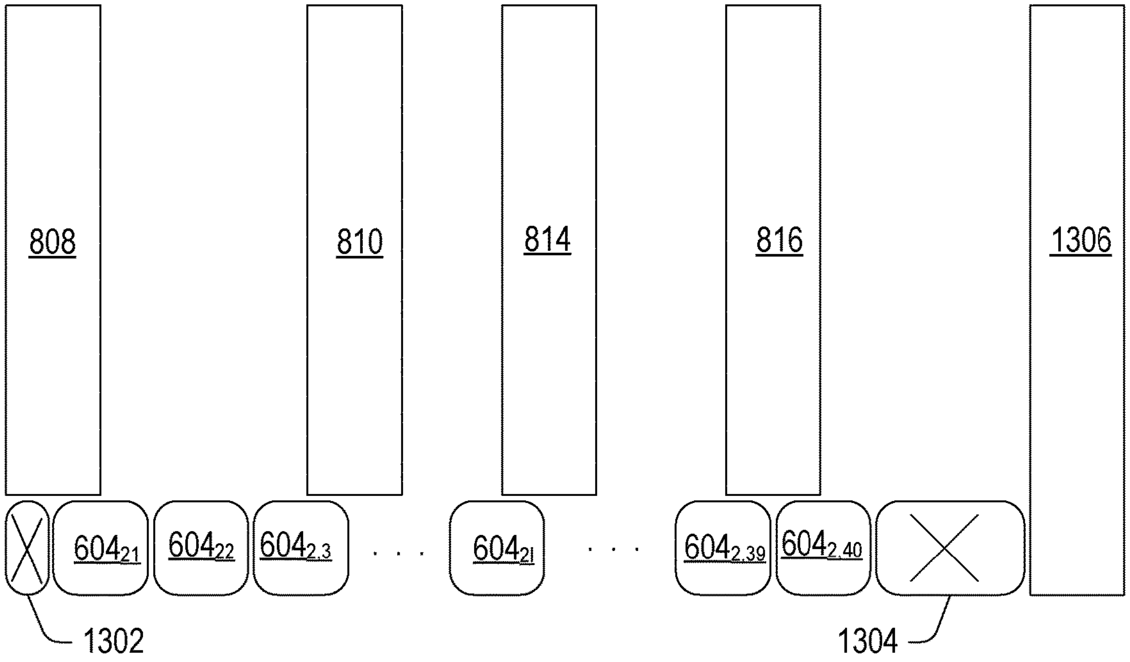
FIG. 13 schematically illustrates yet another arrangement of the septa for the higher energy radiation collimator with respect to the detector pixels, in accordance with an aspect of an embodiment(s) herein.

Relative to FIGS. 8 and/or 9, in FIG. 13, the septa 808, 810 and 816 are all shifted to the left by half a pixel. A first inactive pixel 1302 that is approximately half the size of a detector pixel is added before the first detector pixel of the row (i.e., before the detector pixel $\mathbf{604}_{2,1}$). The septum 808 is now directly aligned between the first inactive pixel 1302 and the pixel $\mathbf{604}_{2,1}$. The septum 810 is now directly aligned between the pixel $\mathbf{604}_{2,3}$ and its neighboring pixel (not shown for consistency with the other figures). The septum 814 is now directly aligned between the pixel $\mathbf{604}_{2,1}$ and its neighboring pixel (not shown for consistency with the other figures). The septum 816 is now directly aligned between the detector pixels $\mathbf{604}_{2,39}$ and pixels $\mathbf{604}_{2,40}$. A second inactive pixel 1304 (with a width one and a half time the width of a detector pixel) is added after the last detector pixel $\mathbf{604}_{2,40}$ along the illustrated single row. A septum 1306 is added next to the inactive pixel 1304, along the illustrated single row, and extended by approximately a height of a detector pixel.

Figure 14:
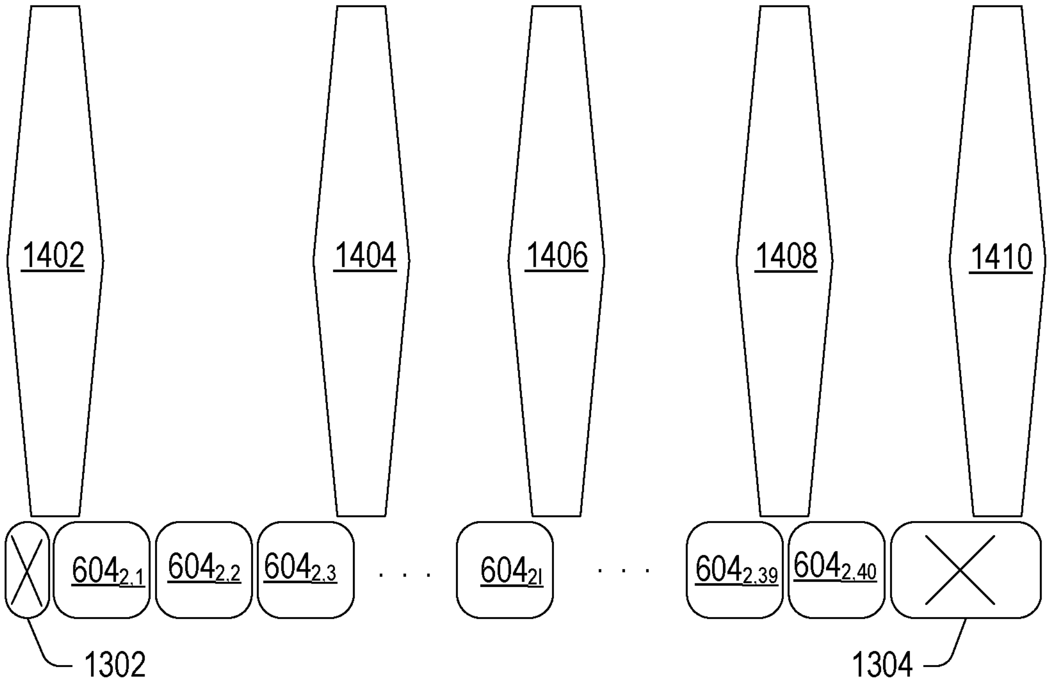
FIG. 14 schematically illustrates still another arrangement of the septa for the higher energy radiation collimator with respect to the detector pixels, in accordance with an aspect of an embodiment(s) herein.

The arrangement in FIG. 14 is substantially similar to the arrangement in FIG. 13, except that the septa are shaped like the septum described in connection with FIG. 10 instead of the septa described in connection with FIGS. 8 and 9. The first inactive pixel 1302 that is approximately half the size of a detector pixel is added before the first detector pixel of the row (i.e., before the detector pixel $\mathbf{604}_{2,1}$). A septum 1402 is directly aligned between the first inactive pixel 1302 and the pixel $\mathbf{604}_{2,1}$. A septum 1404 is directly aligned between the pixel $\mathbf{604}_{2,3}$ and its neighboring pixel (not shown for consistency with the other figures). A septum 1406 is directly aligned between the pixel $\mathbf{604}_{2,1}$ and its neighboring pixel (not shown for consistency with the other figures). A septum 1408 is directly aligned between the detector pixels $\mathbf{604}_{2,39}$ and pixels $\mathbf{604}_{2,40}$. The second inactive pixel 1304 (with a width one and a half time the width of a detector pixel) is added after the last detector pixel $\mathbf{604}_{2,40}$ along the illustrated single row. A septum 1410 is directly aligned with respect to a sub-portion of the second inactive pixel 1304.

Figure 15:
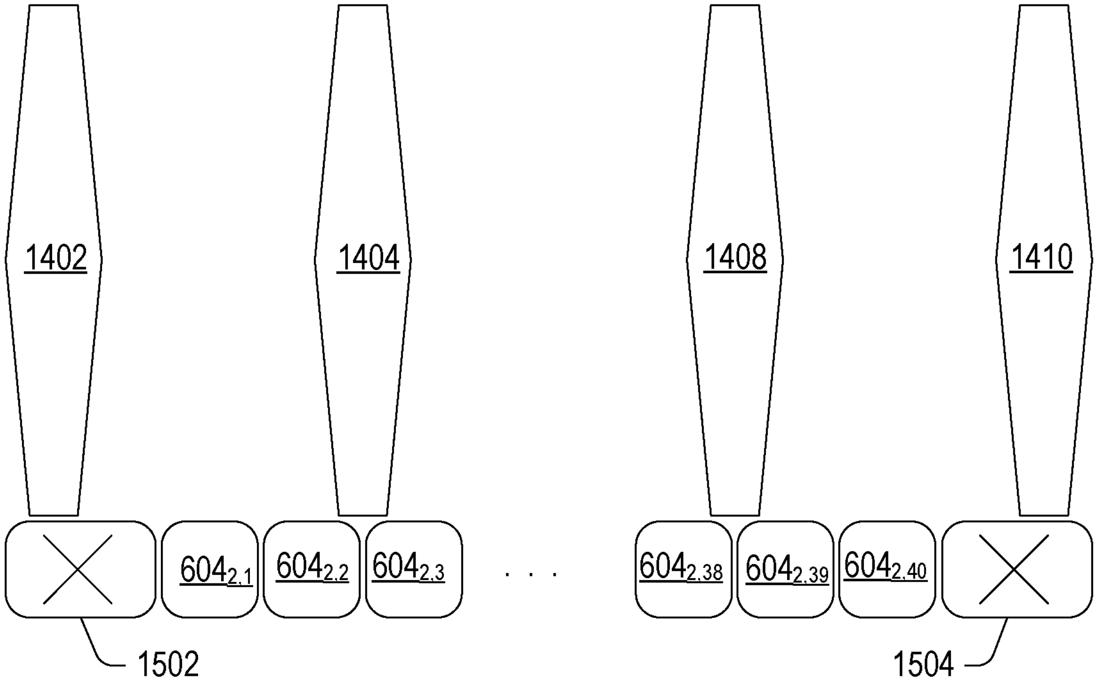
FIG. 15 schematically illustrates another arrangement of the septa for the higher energy radiation collimator with respect to the detector pixels, in accordance with an aspect of an embodiment(s) herein.

FIG. 15 schematically illustrates a symmetrical arrangement. A first inactive pixel 1502 that is approximately one and a half the size of a detector pixel is added before the first detector pixel of the row (i.e., before the detector pixel $\mathbf{604}_{2,1}$). The septum 1402 is directly aligned with respect to a sub-portion of the second inactive pixel 1502. The septum 1404 is now directly aligned between the pixel $\mathbf{604}_{2,2}$ and the pixel $\mathbf{604}_{2,3}$. The septum 1406 is not shown. The septum 1408 is now directly aligned between the detector pixels $\mathbf{604}_{2,38}$ and pixels $\mathbf{604}_{2,39}$. A second inactive pixel 1504 that is approximately a width one and a half times the width of a detector pixel is added after the last detector pixel $\mathbf{604}_{2,40}$ along the illustrated single row. The septum 1410 is directly aligned with respect to a sub-portion of the second inactive pixel 1504.

Figure 16:
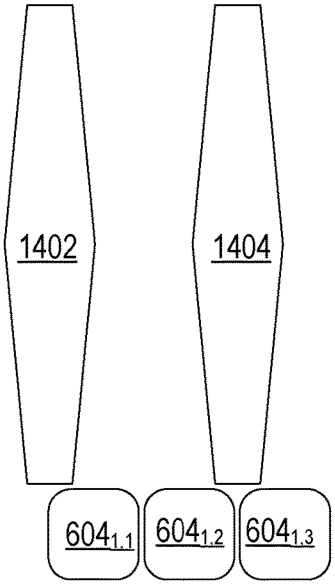
FIG. 16 schematically illustrates another arrangement of the septa for the higher energy radiation collimator with a smaller septa pitch, in accordance with an aspect of an embodiment(s) herein.

The arrangement in FIG. 16 is substantially similar to the arrangement in FIGS. 6 and 7 (i.e., a 2 detector pixel pitch), except that the septa are shaped like the septum described in connection with FIG. 10 instead of the septa described in connection with FIGS. 6 and 7. The septum 1402 is aligned with an edge of the pixel $\mathbf{604}_{1,1}$. The septum 1404 is directly aligned between the pixel $\mathbf{604}_{1,2}$ and the pixel $\mathbf{604}_{1,3}$. The septum 1406 is not shown. The septum 1408 is directly aligned between the detector pixels $\mathbf{604}_{1,38}$ and pixels $\mathbf{604}_{1,39}$. The septum 1410 is aligned with an edge of the pixel $\mathbf{604}_{1,40}$. Note that the configuration of higher energy collimator seen in FIG. 16 is similar to that of the lower energy collimator seen in FIG. 7, yet, the penetration is greatly reduced due to the thicker central septa, and specifically, the fact that the septa are thicket at their center. This allows using similar reconstruction strategies for both high and low energy images. Due to the thick septa of the higher energy collimator seen in FIG. 16, the septa need not be as high to achieve similar resolution. This allows a more compact construction of the collimator and the entire detector unit assembly.

Figure 17:
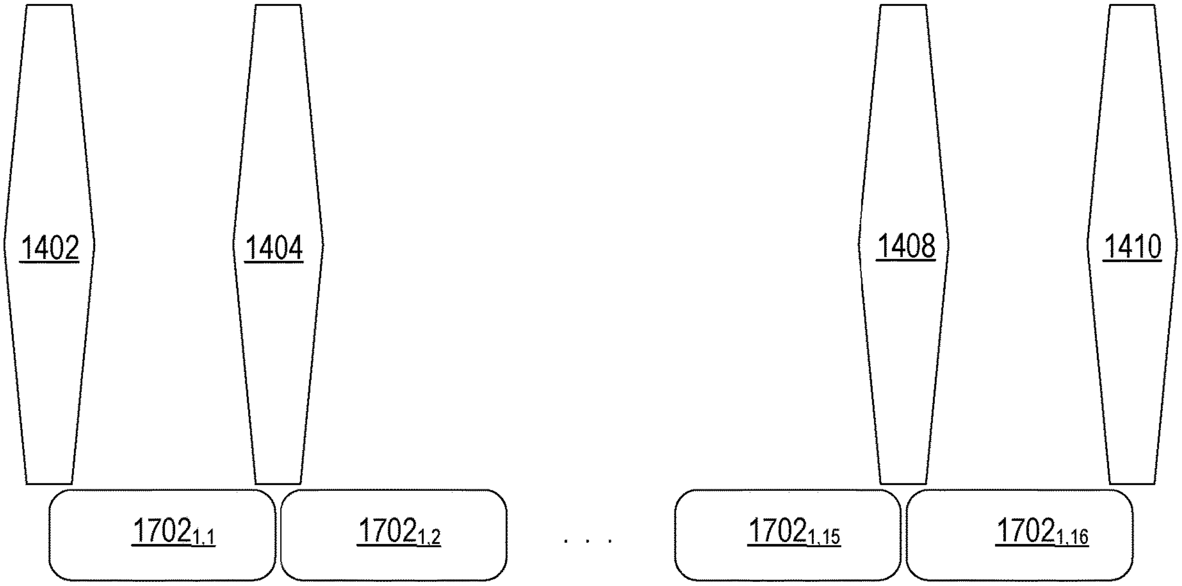
FIG. 17 schematically illustrates another arrangement of the septa for the higher energy radiation collimator with larger detector pixels, in accordance with an aspect of an embodiment(s) herein.

The arrangement in FIG. 17 includes the septum described in FIG. 10 for detector pixels that are 2.5 $mm^2$ with a septa pitch of 1 detector pixel for the 40 $mm^2$ detector module 504. Such a configuration includes include 16×16 (256) detector pixels per module, 1,792 detector pixels where the detector array 302 includes an array of 1×7 modules. In this example, the septum 1402 is aligned with an edge of the pixel $\mathbf{1702}_{1,1}$. The septum 1404 is directly aligned between the pixel $\mathbf{1702}_{1,1}$ and the pixel $\mathbf{1702}_{1,1}$. The septum 1406 is not shown. The septum 1408 is directly aligned between the detector pixels $\mathbf{1702}_{1,15}$ and pixels $\mathbf{1702}_{1,16}$. The septum 1410 is aligned with an edge of the pixel $\mathbf{1702}_{1,16}$. In analogy to the choice of the height of the septa, as detailed in the text related to FIGS. 6-9, the height of the septa seen in FIGS. 10-17 may be similarly selected such that the resolution of the higher energy collimator will be similar or equal to that of the lower energy collimator. Alternatively, in analogy to the choice of the height of the septa, as detailed in the text related to FIGS. 6-9, the heigh of the septa seen in FIGS. 10-17 may be similarly selected such that the sensitivity of the high energy collimator will be similar or equal to that of the low energy collimator.

Figure 18:
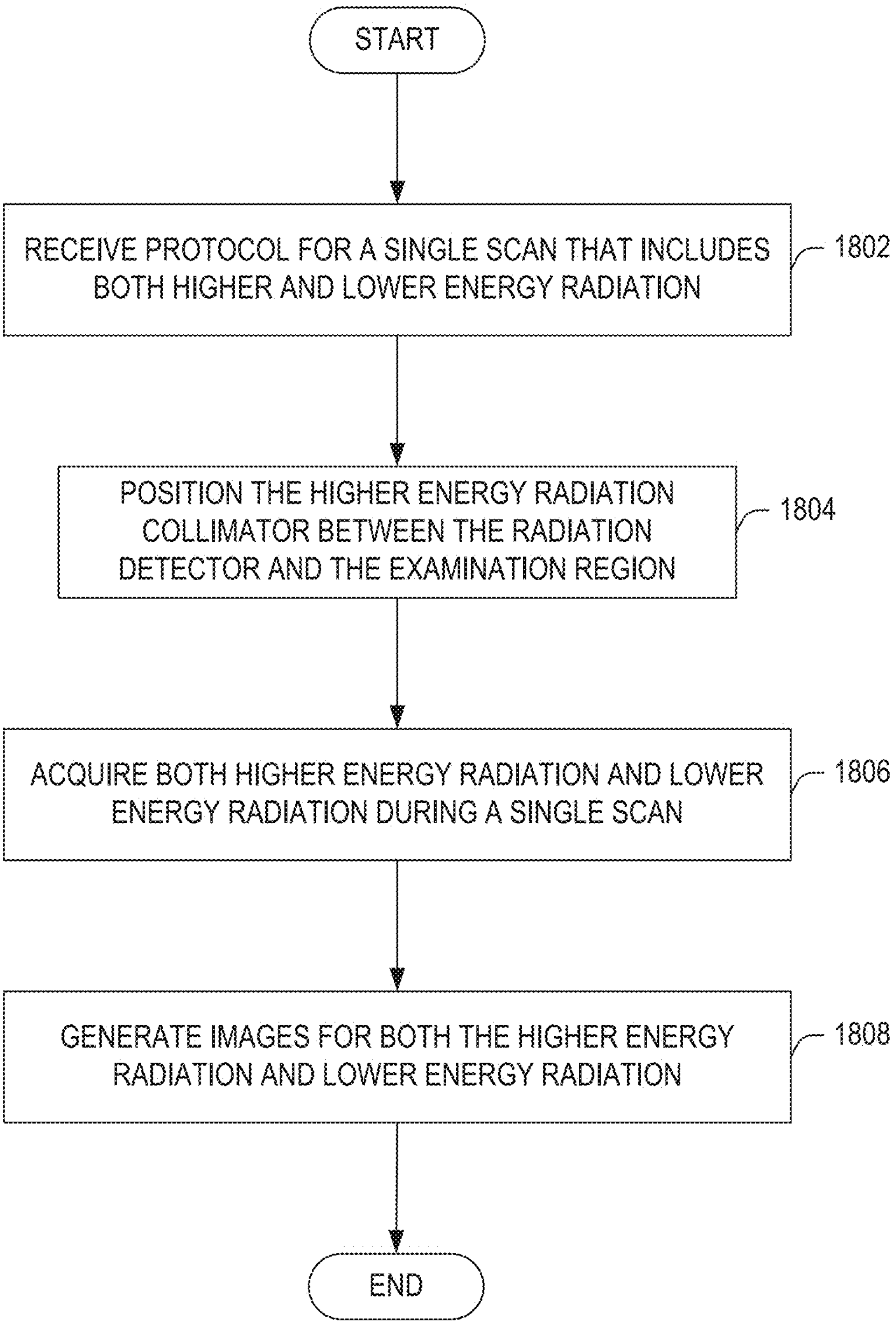
FIG. 18 illustrates a non-limiting example of a flow chart for concurrently acquiring higher energy radiation and lower energy radiation with a higher energy radiation collimator without significantly compromising a spatial resolution for the lower energy radiation or compromising septa penetration for the higher energy radiation, in accordance with an aspect of an embodiment(s) herein.

FIG. 18 illustrates a non-limiting example of a flow chart for a computer-implemented method employing a higher energy radiation collimator for a multi-energy (higher and lower radiation) application. It is to be appreciated that the ordering of the acts in the method is not limiting. As such, other orderings are contemplated herein. In addition, one or more acts may be omitted, and/or one or more additional acts may be included.

At 1802, the imaging system 102 receives in input for an imaging protocol for a single scan that includes acquisitions for both higher energy radiation and lower energy radiation, as described herein and/or otherwise. At 1804, the imaging system 102 positions the higher energy radiation collimator 308 so that it is between the radiation detector 302 and the examination region 106, as described herein and/or otherwise. At 1806, the imaging system 102 acquires both higher energy radiation and lower energy radiation during the single scan, as described herein and/or otherwise. At 1808, the imaging system 102 generates images for both the higher energy radiation and lower energy radiation, as described herein and/or otherwise.

The images can be displayed, archived, etc., as described herein and/or otherwise. As discussed herein, the higher energy radiation collimator 308 is not only configured for higher energy radiation applications, but can also be utilized for multi-energy applications where higher energy radiation and lower energy radiation are concurrently detected, without compromising a spatial resolution for the lower energy radiation or septa penetration for the high energy radiation. In one instance, this provides an acquisition time reduction over a configuration in which separate collimators are utilized, e.g., the higher energy radiation collimator for higher energy radiation and the lower energy radiation collimator for lower energy radiation.

Figure 19:
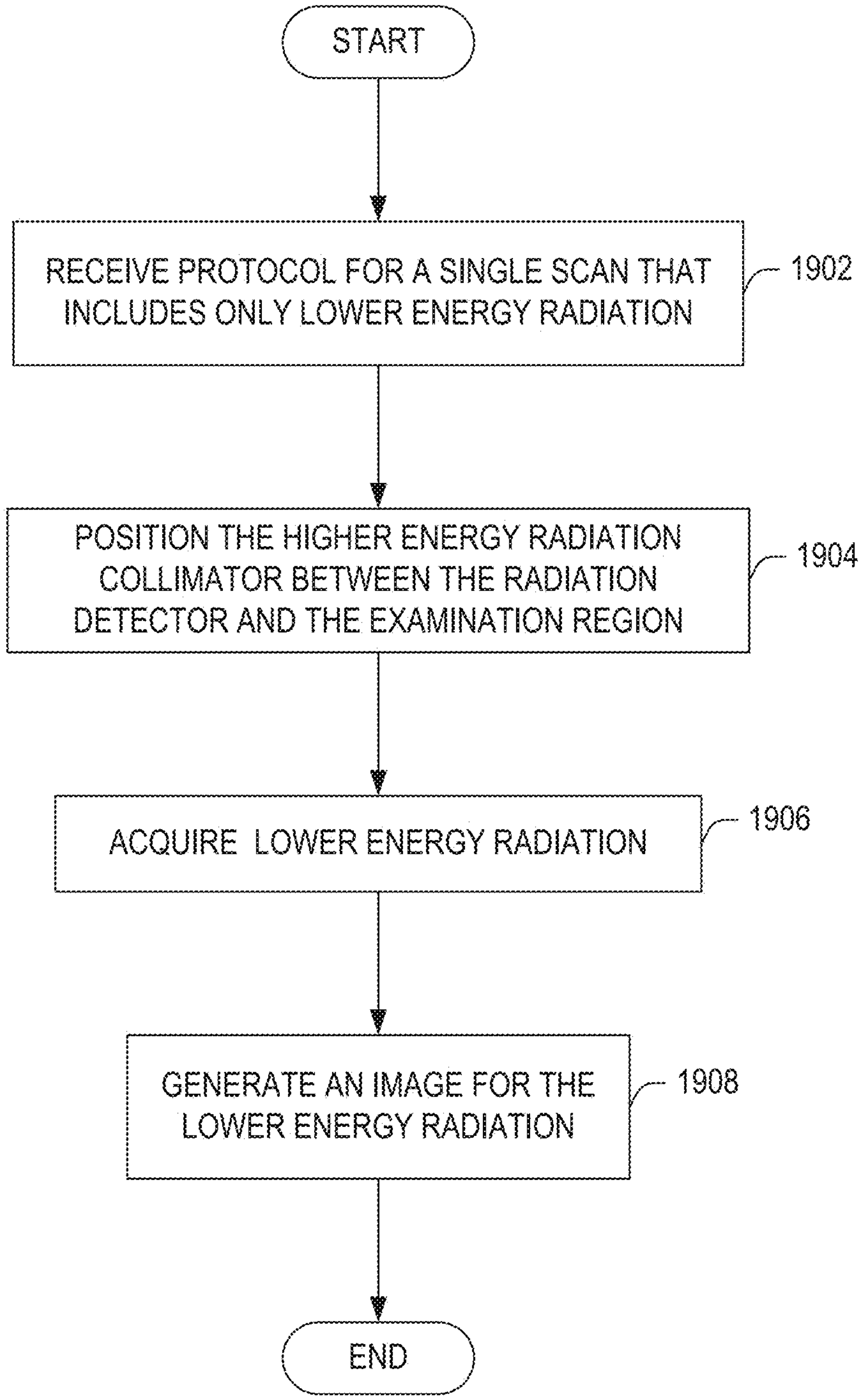
FIG. 19 illustrates another non-limiting example of a flow chart for acquiring higher lower energy radiation with a higher energy radiation collimator without significantly compromising a spatial resolution for the lower energy radiation, in accordance with an aspect of an embodiment(s) herein.

FIG. 19 illustrates a non-limiting example of a flow chart for a computer-implemented method employing a higher energy radiation collimator for all applications. It is to be appreciated that the ordering of the acts in the method is not limiting. As such, other orderings are contemplated herein. In addition, one or more acts may be omitted, and/or one or more additional acts may be included.

At 1902, the imaging system 102 receives in input for an imaging protocol for a single scan that includes acquisitions for a lower energy radiation, as described herein and/or otherwise. At 1904, the imaging system 102 positions the higher energy radiation collimator 308 so that it is between the radiation detector 302 and the examination region 106, as described herein and/or otherwise. Where the imaging system 102 includes only the higher energy radiation collimator 308, act 1904 is omitted. At 1906, the imaging system 102 acquires lower energy radiation during the scan, as described herein and/or otherwise. At 1906, the imaging system 102 generates images for the lower energy radiation, as described herein and/or otherwise.

The images are displayed, archived, etc., as described herein and/or otherwise. As discussed herein, the higher energy radiation collimator 308 is not only configured for higher energy radiation applications, but can also be utilized for multi-energy applications where higher energy radiation and lower energy radiation are concurrently detected, without compromising a spatial resolution for the lower energy radiation or septa penetration for the high energy radiation.

The above can be implemented by way of computer readable instructions, encoded, or embedded on the computer readable storage medium, which, when executed by a computer processor, cause the processor to carry out the described acts or functions. Additionally, or alternatively, at least one of the computer readable instructions is carried out by a signal, carrier wave or other transitory medium, which is not computer readable storage medium.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include such additional elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer". The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present disclosure. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. A single photon emission computed tomography (SPECT) imaging system, comprising:

a detector unit configured to receive photons emitted by a radiopharmaceutical and convert the received photons to projection data, wherein the radiopharmaceutical emits radiation in a higher energy radiation range of interest and a lower energy radiation range of interest, and the detector unit concurrently detects the radiation in the higher and lower energy radiation ranges, a higher energy radiation collimator is positioned between the detector unit and the photons emitted by a radiopharmaceutical, wherein the higher energy radiation collimator is configured for septa penetration for the higher energy radiation of interest without compromising a spatial resolution for the lower energy radiation of interest; and a reconstructor configured to reconstruct a first image from projection data for the higher energy radiation of interest and a second image from projection data for the lower energy radiation of interest.

2. The SPECT imaging system of claim 1, wherein the detector unit includes the higher energy radiation collimator and a lower energy radiation collimator, wherein an aspect ratio for septa of the higher energy radiation collimator is approximately the same as an aspect ratio of septa of the lower energy radiation collimator, and wherein the higher energy radiation collimator is positioned between the detector unit and the photons for higher energy radiation and the lower energy radiation collimator is positioned between the detector unit and the photons for lower energy radiation applications.

3. The SPECT imaging system of claim 2, wherein the aspect ratio for septa of the higher energy radiation collimator and the aspect ratio of septa of the lower energy radiation collimator are within 2.5% of each other.

4. The SPECT imaging system of claim 3, wherein the aspect ratio for septa of the higher energy radiation collimator is a ratio of an aperture length of a septum of the higher energy radiation collimator to a height of the septum of the higher energy radiation collimator, and the aspect ratio of septa of the lower energy radiation collimator is equal to a ratio of an aperture length of a septum of the lower energy radiation collimator to a height of the septum of the higher energy radiation collimator.

5. The SPECT imaging system of claim 2, wherein a spatial resolution of the second image is approximately the same as a spatial resolution of an image reconstructed with lower energy radiation acquired using the lower energy radiation collimator.

6. The SPECT imaging system of claim 2, wherein the detector unit includes a plurality of pixels, a septa pitch of the higher energy radiation collimator is three detector pixels by three detector pixels and a septa pitch of the lower energy radiation collimator is two detector pixels by two detector pixels.

7. The SPECT imaging system of claim 6, wherein a width of a septum of the septa of the higher energy radiation collimator is aligned with a width of a pixel of the plurality of pixels.

8. The SPECT imaging system of claim 2, where septa of the higher energy radiation collimator have planar sides.

9. The SPECT imaging system of claim 2, wherein the lower energy radiation collimator is positioned between the detector unit and the photons emitted by a radiopharmaceutical that emits radiation only in the lower energy radiation range of interest.

10. The SPECT imaging system of claim 1, wherein a spatial resolution of the second image is approximately the same as a spatial resolution of an image reconstructed with lower the energy radiation acquired by a lower energy radiation collimator optimized for lower energy radiation applications.

11. A computer-implemented method, comprising:

positioning a higher energy radiation collimator of a detector assembly that includes both the higher energy radiation collimator and a lower energy radiation collimator between a radiation detector of the detector assembly and an imaging examination region for an imaging protocol that includes both higher and lower energy radiation;

acquiring both radiation in a higher energy radiation range of interest and a lower energy radiation range of interest emitted by a radiopharmaceutical in the imaging examination region; and reconstructing a first image from the higher energy radiation of interest and a second image from the lower energy radiation of interest.

12. The computer-implemented method of claim 11, wherein an aspect ratio for septa of the higher energy radiation collimator is approximately the same as an aspect ratio of septa of the lower energy radiation collimator.

13. The computer-implemented method of claim 12, wherein the aspect ratio for septa of the higher energy radiation collimator and the aspect ratio of septa of the lower energy radiation collimator are within 2.5% of each other.

14. The computer-implemented method of claim 11, further comprising:

positioning the lower energy radiation collimator between the detector of the detector assembly and the imaging examination region for an imaging protocol that includes only the lower energy radiation;

acquiring radiation in the lower energy radiation range of interest; and reconstructing a third image from the lower energy radiation of interest.

15. The computer-implemented method of claim 14, where a spatial resolution of the second image and a spatial resolution of the third image are approximately the same.

16. A non-transitory computer readable medium encoded with computer executable instructions, which, when executed by a processor, cause the processor to: position a higher energy radiation collimator of a detector assembly that includes both the higher energy radiation collimator and a lower energy radiation collimator between a detector unit of the detector assembly and an imaging examination region for an imaging protocol that includes both higher and lower energy radiation; acquire both radiation in a higher energy radiation range of interest and a lower energy radiation range of interest emitted by a radiopharmaceutical in the imaging examination region; and reconstruct a first image from the higher energy radiation of interest and a second image from the lower energy radiation of interest.

17. The non-transitory computer readable medium of claim 16, wherein an aspect ratio for septa of the higher energy radiation collimator is approximately the same as an aspect ratio of septa of the lower energy radiation collimator.

18. The non-transitory computer readable medium of claim 17, wherein the aspect ratio for septa of the higher energy radiation collimator and the aspect ratio of septa of the lower energy radiation collimator are within 2.5% of each other.

19. The non-transitory computer readable medium of claim 16, wherein the computer executable instructions further cause the processor to: position the lower energy radiation collimator between the detector unit of the detector assembly and the imaging examination region for an imaging protocol that includes only the lower energy radiation; acquire radiation in the lower energy radiation range of interest; and reconstruct a third image from the lower energy radiation of interest.

20. The non-transitory computer readable medium of claim 19, where a spatial resolution of the second image and a spatial resolution of the third image are approximately the same.

* * * * *